(12) United States Patent
O'Shea et al.

(10) Patent No.: US 9,193,952 B2
(45) Date of Patent: Nov. 24, 2015

(54) METHODS FOR REGULATING NEURAL DIFFERENTIATION

(71) Applicant: The Regents of the University of Michigan, Ann Arbor, MI (US)

(72) Inventors: Kathy Sue O'Shea, Ann Arbor, MI (US); Maria Morell, Granada (ES); Yao-Chang Tsan, Taipei (TW)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 14/153,720

(22) Filed: Jan. 13, 2014

(65) Prior Publication Data

US 2014/0134738 A1 May 15, 2014

Related U.S. Application Data

(62) Division of application No. 13/213,848, filed on Aug. 19, 2011, now Pat. No. 8,642,342.

(60) Provisional application No. 61/471,368, filed on Apr. 4, 2011, provisional application No. 61/375,154, filed on Aug. 19, 2010.

(51) Int. Cl.
*C12N 5/079* (2010.01)
*C12Q 1/68* (2006.01)
*C12N 15/11* (2006.01)

(52) U.S. Cl.
CPC ............ *C12N 5/0622* (2013.01); *C12N 15/111* (2013.01); *C12Q 1/6897* (2013.01); *C12N 2310/141* (2013.01); *C12N 2320/10* (2013.01); *C12N 2320/30* (2013.01); *C12N 2501/65* (2013.01); *C12N 2506/02* (2013.01)

(58) Field of Classification Search
None
See application file for complete search history.

(56) References Cited

U.S. PATENT DOCUMENTS

| | | | |
|---|---|---|---|
| 8,642,342 B2 | 2/2014 | O'Shea et al. | |
| 2006/0185027 A1* | 8/2006 | Bartel et al. | 800/14 |
| 2007/0292878 A1 | 12/2007 | Raymond | |
| 2008/0050744 A1 | 2/2008 | Brown et al. | |
| 2008/0171715 A1 | 7/2008 | Brown et al. | |
| 2008/0176766 A1 | 7/2008 | Brown et al. | |
| 2009/0105174 A1 | 4/2009 | Jayasena | |
| 2009/0123912 A1 | 5/2009 | Raymond | |
| 2009/0176723 A1 | 7/2009 | Brown et al. | |

OTHER PUBLICATIONS

Hennessy et al., Identification of microRNAs with a role in glucose stimulated insulin secretion by expression profiling of MIN6 cells; Biochemical and Biophysical Research, 2010. vol. 396, pp. 457-462.*

Berger et al., Inhibition of micro-RNA-induced RNA silencing by 2'-o-methyl oligonucleotides in Drosophila S2 cells, *In Vitro Cell. Dev. Biol. Animal*, 2005, 41:12-18.
Ebert et al., "MicroRNA sponges: competitive inhibitors of small RNAs in mammalian cells," *Nat. Methods*, 2007, 4(9):721-726.
Flynt et al., "Micro RNAs may have a crucial role in the signaling processes that govern vertebrate cell fate decisions," *Nature Genetics*, 2007, 39:259-263.
Huang et al., "MicroRNA expression profiling during neural differentiation of mouse embryonic carcinoma P19 cells," *Acta Biochim Biophys Sin*, 2009, pp. 231-236.
Ivey & Srivastava, "MicroRNAs as regulators of differentiation and cell fate decisions," *Cell Stem Cell*, 2010, 7:36-41.
Krutzfeldt et al., "Silencing of microRNAs in vivo with 'antagomirs'," *Nature*, 2005, 438:685-689.
Martinez & Gregory, "MicroRNA gene regulatory pathways in the establishment and maintenance of ESC identity," *Cell Stem Cell*, 2010, 7:31-35.
Ørom et al., "LNA-modified oligonucleotides mediate specific inhibition of microRNA function," *Gene*, 2006, 372:137-141.
Patil et al., "DNA-based Therapeutics and DNA Delivery Systems: A Comprehensive Review," *AAPS J.*, 2005, 7(1):E61-E77.
Wheeler et al., "Identification of new central nervous system specific mouse microRNAs," *FEBS Lett.*, Apr. 17, 2006, 580(9):2195-200, Epub Mar. 20, 2006.
Zhao et al., "A feedback regulatory loop involving microRNA-9 and nuclear receptor TLX in neural stem cell fate determination," *Nature Structural & Molecular Biology*, 2009, 16:365-371, Published online: Mar. 29, 2009.
Hennessy et al., "Identification of microRNAs with a role in glucose stimulated insulin secretion by expression profiling of MIN6 cells," *Biochem Biophys Res Commun.*, 396(2):457-462, Epub Apr. 24, 2010.
Nakashima et al., "MIN6 is not a pure beta cell line but a mixed cell line with other pancreatic endocrine hormones," *Endocr J.*, 56(1):45-53, Epub Oct. 9, 2008.
GenBank Accession No. NM_021543 dated Mar. 7, 2012, 4 pages.
GenBank Accession No. NM_001044386 dated Mar. 24, 2012, 5 pages.
GenBank Accession No. NM_053242 dated Apr. 22, 2012, 6 pages.
GenBank Accession No. NM_054043 dated Apr. 22, 2012, 5 pages.
GenBank Accession No. NM_172303 dated Apr. 23, 2012, 5 pages.
GenBank Accession No. NM_178880 dated Apr. 29, 2012, 9 pages.
GenBank Accession No. NM_008008 dated May 5, 2012, 4 pages.
GenBank Accession No. NM_008665 dated May 5, 2012, 6 pages.
GenBank Accession No. NM_001042660 dated May 12, 2012, 4 pages.
GenBank Accession No. NM_001083967 dated May 12, 2012, 7 pages.
GenBank Accession No. NM_008342 dated May 12, 2012, 4 pages.

(Continued)

*Primary Examiner* — Jennifer Dunston
*Assistant Examiner* — Addison D Ault
(74) *Attorney, Agent, or Firm* — Fish & Richardson P.C.

(57) ABSTRACT

Methods of producing populations of predominantly astrocytes, neurons or oligodendrocytes are provided. In addition, methods of treating mammals having astroglial tumors, oligodendrocyte tumors, or neuronal tumors are provided.

5 Claims, 16 Drawing Sheets

(56) References Cited

OTHER PUBLICATIONS

GenBank Accession No. NM_027642 dated May 12, 2012, 5 pages.
GenBank Accession No. NM_001083316 dated May 19, 2012, 6 pages.
GenBank Accession No. NM_008702 dated May 27, 2012, 5 pages.
GenBank Accession No. NM_009233 dated May 27, 2012, 4 pages.
GenBank Accession No. NM_009322 dated May 27, 2012, 4 pages.
GenBank Accession No. NM_010488 dated May 27, 2012, 4 pages.
GenBank Accession No. NM_020505 dated May 27, 2012, 5 pages.
GenBank Accession No. NM_144841 dated Jun. 2, 2012, 3 pages.

\* cited by examiner

FIGURE 1

```
                              a   a              a  u   a
        c              ug        ug     c  - uuu
 g                       ucugug     guucg
  ggua ugagga  aggu    |||||||    |||||
  ||||| |||||||  ||||    agacac     uaagc
a ccau_ aacuuu u  uccg gu        au a  a g uaa
                    g                      a
```

SEQ ID NO.:2

SEQUENCE LISTING

<160> NUMBER OF SEQ ID NOS: 2

<210> SEQ ID NO 1
<211> LENGTH: 21
<212> TYPE: RNA
<213> ORGANISM: Homo sapiens

<400> SEQUENCE: 1
aauauaacac agauggccug u                                             21

<210> SEQ ID NO 2
<211> LENGTH: 81
<212> TYPE: RNA
<213> ORGANISM: Homo sapiens

<400> SEQUENCE: 2
ggguacuuga ggagagguug ucugugauga guucgcuuua uuaaugacga auauaacaca   60
gauggccugu uuucaauacc a                                             81

METHODS FOR REGULATING NEURAL DIFFERENTIATION

CROSS-REFERENCE TO RELATED APPLICATIONS

This application is a Divisional application of, and claims the benefit of priority under 35 U.S.C. §121 to, U.S. application Ser. No. 13/213,848, filed on Aug. 19, 2011, which claims the benefit of priority under 35 U.S.C. §119(e) to U.S. application Ser. No. 61/471,368, filed Apr. 4, 2011, and U.S. application Ser. No. 61/375,154, filed Aug. 19, 2010.

FEDERALLY SPONSORED RESEARCH OR DEVELOPMENT

This invention was made with government support under NS048187 awarded by the National Institutes of Health. The Government has certain rights in the invention.

TECHNICAL FIELD

This document provides methods related to differentiation of stem cells (e.g., neural stem cells). For example, this document provides methods for differentiating stem cells into predominantly astrocytes or predominantly neurons and oligodendrocytes.

BACKGROUND

Regulation of gene expression during development occurs at multiple levels as indicated by the recent identification of numerous cis-regulatory sequences, transcription complexes, microRNAs (miRNAs), and additional classes of non-coding RNAs. miRNAs are small, single-stranded RNAs that play important roles in proliferation, differentiation, tumorigenesis, and apoptosis via their ability to silence target genes. miRNAs function primarily as repressors of gene expression, typically acting at the level of translational regulation of gene expression. miRNAs can also promote mRNA degradation and, in quiescent cells, activate translation. The ability of miRNAs to regulate large sets of target genes may provide "developmental switches" during lineage differentiation of various cell types including stem cells.

SUMMARY

In one aspect, a method of producing a population of predominantly astrocytes is provided. Such a method typically includes overexpressing miRNA-410 in a population of stem cells or downstream precursor cells. Generally, the overexpressing miRNA-410 results in differentiation of the cells into a population of predominantly astrocytes.

In certain embodiment, overexpressing miRNA-410 comprises introducing a nucleic acid molecules comprising a promoter operably linked to a DNA sequence encoding miRNA-410. In some embodiments, the promoter is an inducible promoter. In some embodiments, the method is performed in vitro. In some embodiments, the stem cells are neural stem cells.

In another aspect, a method of producing a population of predominantly astrocytes is produced. Such methods typically include contacting a population of stem cells or downstream precursor cells with miRNA-410. Generally, the contacting step results in differentiation of the cells into a population of predominantly astrocytes.

In certain embodiments, the contacting further comprises using a lipid-based delivery system. In certain embodiments, the method is performed in vitro. In some embodiments, the stem cells are neural stem cells.

In yet another aspect, a method of producing a population of predominantly neurons and oligodendrocytes is provided. Such a method typically includes inhibiting the expression or activity of miRNA-410 in a population of stem cells or downstream precursor cells. Generally, the inhibiting expression or activity of miRNA-410 results in differentiation of the cells into a population of predominantly neurons and oligodendrocytes.

In certain embodiments, the inhibiting comprises using (e.g., contacting cells with) an antagomir specific for miRNA-410. In certain embodiments, the inhibiting comprises using (e.g., contacting cells with) a 2-O-methyl oligoribonucleotide (2-O-Me-RNA) specific for miRNA-410. In certain embodiments, inhibiting comprises using (e.g., contacting cells with) a morpholino oligonucleotide complementary to miRNA-410. In certain embodiments, the inhibiting comprises using (e.g., contacting cells with) an miRNA sponge. In certain embodiments, the inhibiting comprises using (e.g., contacting cells with) LNA oligonucleotides.

In some embodiments, the method is performed in vitro. In some embodiments, the stem cells are neural stem cells. In some embodiments, the method further includes contacting the cells with noggin.

In still another aspect, a method for identifying a compound that inhibits or induces the activity of miRNA-410 is provided. Such a method typically includes contacting a nucleic acid molecule with a test compound in the presence of miRNA-410, wherein the nucleic acid molecule comprises a promoter operably linked to nucleic acid encoding a miRNA-410 binding site operably linked to nucleic acid encoding a reporter protein. Generally, an increase in the amount of reporter protein is indicative of a compound that inhibits the activity of miRNA-410, and a decrease in the amount of reporter protein is indicative of a compound that increases the activity of miRNA-410. In certain embodiments, the nucleic acid molecule is comprised within a host cell.

In yet another aspect, a method of treating an animal having an astroglial tumor is provided. Such a method typically includes contacting the tumor with a compound that inhibits the expression or activity of miRNA-410, wherein the contacting promotes differentiation of cells in the astroglial tumor. In certain embodiments, the contacting comprises direct injection of the compound into the tumor. Representative compounds that inhibit the expression or activity of miRNA-410 include, for example, an antagomir specific for miRNA-410, a morpholino oligonucleotide complementary to miRNA-410, 2-O-methyl oligoribonucleotide (2-O-Me-RNA) specific for miRNA-410, LNA oligonucleotides, and the sponge. Representative tumors include a glioma, astrocytoma (protoplasmic, gemistocytic, fibrillary), pilocytic astrocytoma, subependymal astrocytoma, pleomorphic xanthoastrocytoma, and neurofibromas.

In still another aspect, a method of treating an animal having a neuronal tumor is provided. Such a method typically contacting the tumor with miRNA-410 or a compound that increases the expression or activity of miRNA-410, wherein the contacting promotes differentiation of cells in the neuronal tumor. In certain embodiments, the contacting comprises direct injection of the miRNA-410 or the compound into the tumor. A representative compound that increases the expression or activity of miRNA-410 is a nucleic acid molecule that includes a promoter operably linked to a miRNA-410 DNA. Representative neuronal tumors include, for example, neuroblastoma, medulloblastoma, retinoblastoma, gangliocytoma, neurocytoma, and ependymoblastoma.

In still another aspect, a method of treating an animal having an oligodendrocyte tumor is provided. Such a method typically contacting the tumor with miRNA-410 or a compound that increases the expression or activity of miRNA-410, wherein the contacting promotes differentiation of cells in the oligodendrocyte tumor. In certain embodiments, the contacting comprises direct injection of the miRNA-410 or the compound into the tumor. A representative compound that increases the expression or activity of miRNA-410 is a nucleic acid molecule that includes a promoter operably linked to a miRNA-410 DNA. Representative oligodendrocyte tumors include, for example, oligoastrocytomas and oligodendrogliomas.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is a schematic depicting the hairpin structure of miR-410.

DETAILED DESCRIPTION

Figure 2:
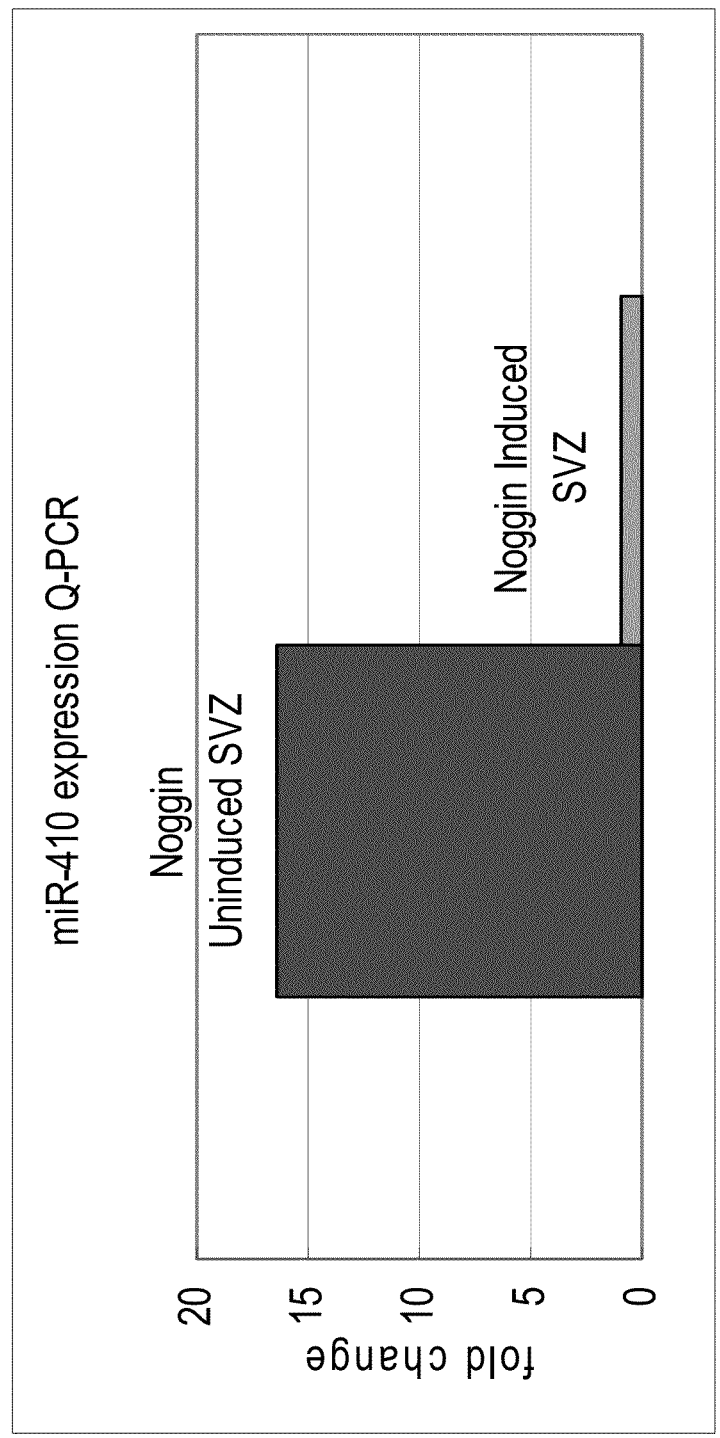
FIG. 2 is a bar graph demonstrating that miR-410 expression is down-regulated 16-fold after noggin expression in the adult subventricular zone (SVZ).

This disclosure describes a novel regulatory role for miRNA-410. As described herein, miRNA-410 plays a critical role in controlling the differentiation of stem cells (e.g., neural stem cells) or downstream precursor cells (e.g., neuronal or glial precursor cells) into predominantly astrocytes or predominantly neurons and oligodendrocytes.

MicroRNAs

MicroRNAs (miRNAs) are short (20-24 nt) non-coding RNAs that play a role in post-transcriptional regulation of gene expression in multicellular organisms by affecting both the stability and translation of mRNAs. miRNAs can be transcribed by RNA polymerase II as part of capped and poly-adenylated primary transcripts (pri-miRNAs) that can be either protein-coding or non-coding. miRNAs also can be transcribed by RNA polymerase III as non-coding RNA transcripts. The primary transcript is cleaved by the Drosha ribonuclease III enzyme to produce an approximately 70-nt stem-loop precursor miRNA (pre-miRNA), which is further cleaved by the cytoplasmic Dicer ribonuclease to generate the mature miRNA and antisense miRNA star (miRNA*) products. The mature miRNA is incorporated into a RNA-induced silencing complex (RISC), which recognizes target messenger RNAs through imperfect base pairing with the miRNA and most commonly results in translational inhibition or destabilization of the target messenger RNA.

Over 650 miRNAs are known in humans and, like transcription factors, a single miRNA can regulate the expression of numerous genes. This effect generally occurs through direct Watson-Crick base-pairing of a small ~22 nucleotide mature miRNA to the 3' UTR of partially complimentary messenger RNAs, largely involving the 5' region of the miRNA known as the seed sequence. Interaction of the miRNA with cognate messenger RNAs typically results in either destabilization or suppressed translation of the messenger RNA targets. Like transcription factors, the spatial and temporal expression of miRNAs is highly regulated and responsive to changes in cellular status. See, for example, Ivey & Srivastava, 2010, *Cell Stem Cell*, 7:36-41; and Martinez & Gregory, 2010, *Cell Stem Cell*, 7:31-5.

miRNA-410 has been identified in a number of mammals (e.g., *Homo sapiens, Mus musculus, Rattus norvegicus, Macaca mulatta, Canis familiaris, Pan troglodytes, Bos taurus, Equus caballus*, and *Pongo pygmaeus*), and the mature sequence is 100% identical across species. The mature sequence of mammalian miRNA-410 is 5'-AAU AUA ACA CAG AUG GCC UGU-3' (SEQ ID NO:1), with the seed sequence located at positions 2-8 of SEQ ID NO:1.

A modified mature miRNA-410 sequence can be used in the methods described herein provided that the modified mature miRNA-410 still retains function (i.e., the modification does not abrogate function). Those of skill in the art would understand that modifications outside of the seed region would be the most likely to result in a sequence that retains function. Modifying a mature miRNA-410 sequence at two nucleotide positions (e.g., outside of the seed sequence) results in a sequence having about 90% sequence identity to SEQ ID NO:1, while modifying a mature miRNA-410 sequence at a single nucleotide (e.g., outside of the seed sequence) results in a sequence having about 95% sequence identity to SEQ ID NO:1. Thus, in addition to miRNA-410 (i.e., SEQ ID NO:1), a nucleic acid having at least 90% sequence identity (e.g., at least 95% sequence identity) to miRNA-410 (i.e., a modified miRNA-410) can be used in the methods described herein.

Percent sequence identity is calculated by aligning two sequences and determining the number of identical matches of nucleotides between the two sequences. The number of identical matches is divided by the length of the aligned region (i.e., the number of aligned nucleotides) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region. It is noted that the percent identity value is usually rounded to the nearest integer, and that the length of the aligned region is always an integer. The alignment of two or more sequences to determine percent sequence identity is performed using the algorithm described by Altschul et al. (1997, *Nucleic Acids Res.*, 25:3389 3402), which is incorporated into BLAST (basic local alignment search tool) programs, available at ncbi.nlm.nih.gov on the World Wide Web. When utilizing BLAST programs to calculate the percent identity between two sequences, the default parameters of the programs are used.

As used herein, an "isolated" nucleic acid is a nucleic acid that is separated from other nucleic acids that are usually associated with the reference nucleic acid. Thus, an "isolated" nucleic acid includes, without limitation, a nucleic acid molecule that is free of sequences that naturally flank one or both ends of the nucleic acid in the genome of the organism from which the isolated nucleic acid molecule is derived. An isolated nucleic acid can be introduced into a vector (e.g., a cloning vector, or an expression vector) for convenience of manipulation or to generate a fusion nucleic acid molecule. In addition, an isolated nucleic acid can be an engineered nucleic acid such as a recombinant or synthetic nucleic acid. Isolated nucleic acids can be obtained using techniques routine in the art including, without limitation, recombinant nucleic acid technology, and/or a polymerase chain reaction (PCR). General PCR techniques are described, for example in *PCR Primer: A Laboratory Manual*, Dieffenbach & Dveksler, Eds., Cold Spring Harbor Laboratory Press, 1995. Recombinant nucleic acid techniques include, for example, restriction enzyme digestion and ligation. Isolated nucleic acids also can be chemically synthesized, and also can be obtained by mutagenesis (e.g., site-directed mutagenesis).

Differentiation of Stem Cells or Downstream Precursor Cells into Predominantly Astrocytes or Predominantly Neurons and Oligodendrocytes As this disclosure demonstrates, an increase in the amount or activity of miRNA-410 causes stem cells or downstream precursor cells to differentiate into a population of predominantly astrocytes. As used herein, a population that is predominantly astrocytes refers to a population of cells that is at least about 55% (e.g., at least about 60%, 70%, 75%, 80%, 85%, 90%, 95%, or at least about 99%) astrocytes. As those skilled in the art would understand, the amount or activity of miRNA-410 can be increased by delivering the miRNA-410 directly to cells and/or by overexpressing the DNA that encodes miRNA-410 in cells.

As used herein, stem cells or downstream precursor cells refer to cells that are able to differentiate into more than one different type of cell. Generally, in the progression of differentiation, precursor cells are downstream of (i.e., more differentiated than) stem cells. For purposes herein, embryonic stem (ES) cells have multi-lineage differentiation capacity and are not restricted to the neural lineage, while neural stem cells and neuronal or glial precursor cells refer to cells that naturally have the capability of differentiating into neurons, astrocytes, and oligodendrocytes. Neural stem cells usually are identified by the expression of glial fibrillary acidic protein (GFAP) and nestin and by the ability to differentiate into oligodendrocytes, neurons, and astrocytes. Those of skill in the art would understand that other stem cells can be used in the methods described herein including, without limitation, induced pluripotent stem cells (iPSC).

miRNA-410 can be delivered directly to stem cells or downstream precursor cells using a number of methods routine in the art. For example, cells can be electroporated with the miRNA-410 (see, for example, Andreason & Evans, 1988, *Biotechniques*, 6(7):650-60), or the miRNA-410 can be introduced into cells using lipid-based delivery systems, nanoparticle delivery systems, or viral-based delivery systems. See, for example, Patil et al., 2005, *AAPS J.*, 7(1):E61-E77. In addition, DNA encoding the miRNA-410 can be overexpressed in cells using routine methods. For example, DNA encoding miRNA-410 can be cloned into an expression vector operably linked to an appropriate promoter, and the expression vector can be introduced into cells using any of the methods already discussed (e.g., electroporation, lipid-based delivery systems, nanoparticle delivery systems, and viral-based delivery systems).

Expression vectors for over-expressing miRNA-410 are commercially available or can be produced by recombinant DNA technology methods routine in the art. An expression vector containing a DNA encoding miRNA-410 typically will have a promoter (e.g., constitutive or inducible) operably linked to the DNA encoding miRNA-410. Many constitutive and inducible promoters are known in the art. As used herein, "operably linked" means that a promoter and/or other regulatory element(s) are positioned in a vector relative to a DNA encoding miRNA-410 in such a way as to direct or regulate expression of the miRNA-410. It would be understood by those skilled in the art that the miRNA-410 or the DNA encoding the miRNA-410 can be homologous to the stem cells or downstream precursor cells (i.e., from the same mammalian species) or heterologous to the stem cells or downstream precursor cells (i.e., from a different mammalian species). An expression vector also may include sequences such as those encoding a selectable marker (e.g., an antibiotic resistance gene).

The amount or activity of miRNA-410 can be increased by increasing (e.g., inducing) one or more of the biological inducers of miRNA-410. For example, bone morphogenic proteins (BMPs) could increase the amount or activity of miRNA-410, thereby increasing the differentiation of the stem cells or downstream precursor cells into astrocytes. As indicated herein, the methods described herein to increase the amount of activity of miRNA-410 (e.g., direct delivery of miRNA-410, overexpression of the DNA encoding miRNA-410, or induction of miRNA-410) can be used in any combination. It is expected that using multiple means to increase the amount or activity of miRNA-410 will increase the number of astrocytes relative to other cells. That is, using multiple means to increase the amount or activity of miRNA-410, it is expected that a substantially pure population of astrocytes can be produced. As used herein, a substantially pure population of astrocytes refers to a population of cells that is at least 95% (e.g., at least 96%, 97%, 98%, 99% or 100%) astrocytes.

As this disclosure also demonstrates, a decrease in the amount or activity of miRNA-410 causes stem cells or downstream precursor cells to differentiate into a population of predominantly neurons and oligodendrocytes. As used herein, a population of predominantly neurons and oligonucleotides refers to a population of at least about 35% (e.g., at least about 40%, 45%, 50%, 55%, 60%, 65%, 70% or 75%) neurons and at least about 4% (e.g., at least about 5%, 6%, 7%, 8%, 9%, or 10%) oligodendrocytes. Significantly, by decreasing the amount or activity of miRNA-410, the number of oligodendrocytes can be increased three-fold or more. As indicated herein, the amount of activity of miRNA-410 can be decreased by increasing (e.g., inducing) one or more of the biological repressors of miRNA-410. For example, noggin can decrease the amount or activity of miRNA-410, thereby increasing the differentiation of the stem cells or downstream precursor cells into neurons and oligodendrocytes.

As those skilled in the art would understand, the amount or activity of miRNA-410 can be decreased by using any number of different methods that have been developed. For example, antagomirs specific for miRNA-410 (see, for example, Krutzfeldt et al., 2005, Nature, 438:685-9), 2-O-methyl oligoribonucleotides (2-O-Me-RNA) specific for miRNA-410 (see, for example, Berger et al., 2005, In Vitro Cell. Dev. Biol. Animal, 41:12-8), or morpholino oligonucleotides complementary to miRNA-410 (see, for example, Flynt et al., 2007, Genetics, 39:259-63) can be used. Further, LNA oligonucleotides (see, for example, Ørom et al., 2006, Gene, 372:137-41) or the "miRNA sponge" (see, for example, Ebert et al., 2007, Nat. Methods, 4(9):721-6) can be used to decrease the amount or activity of miRNA-410 in cells.

The population of predominantly astrocytes, the population of predominantly oligodendrocytes, or the population of predominantly neurons can be used in a variety of methods. For example, the populations of predominantly oligodendrocytes, astrocytes or neurons can be used in drug testing or screening (see below), or the populations of predominantly oligodendrocytes, astrocytes or neurons can be used in cell therapies for treating diseases associated with a loss, damage or deterioration of oligodendrocytes, astrocytes or neurons. Diseases associated with neuronal loss or damage include, for example, lisencephaly, Rhett's syndrome, hydrocephalus, stroke, and traumatic brain injury (TBI); diseases associated with oligodendrocyte loss or damage include, for example, multiple sclerosis, demyelinating disease, leukodystrophies, and agenesis of the corpus callosum; and diseases associated with astrocyte loss or damage include, for example, spinal cord injuries, diseases of the blood brain barrier or anomalies of cell migration such as lisencephaly and hydrocephalus.

Methods of Screening for Compounds that Increase or Decrease the Amount or Activity of miRNA-410

The results described herein regarding the effects of miRNA-410 on stem cells or downstream precursor cells also can be used to screen for compounds that increase or decrease the amount or activity of miRNA-410 (e.g., functional miRNA-410). For example, a nucleic acid molecule can be produced that includes a promoter operably linked to nucleic acid encoding a miRNA-410 binding site operably linked to nucleic acid encoding a reporter protein. Such a nucleic acid molecule can be introduced into host cells (e.g., HeLa cells, 293T cells) using routine methods (e.g., electroporation, lipid-based delivery systems, nanoparticle delivery systems, and viral-based delivery systems), and the host cells can be contacted with a test compound. It would be apparent to those skilled in the art that an increase in the amount of reporter protein in the host cells indicates that the test compound reduces the amount or activity of miRNA-410, and a decrease in the amount of reporter protein in the host cells indicates that the test compound increases the amount or activity of miRNA-410.

As discussed herein, promoters to drive expression of a DNA sequence are well known in the art. Promoters suitable for detecting an increase in a reporter protein or a decrease in a reporter protein would be known to those skilled in the art. Reporter proteins, as well as the nucleic acids encoding those reporter proteins, also are well known in the art and include, by way of example, β-galactosidase, luciferase, chloramphenyl acetyltransferase (CAT), green fluorescent protein (GFP) or variants thereof, and mCherry.

In another embodiment, a test compound can be screened for the ability to increase or decrease the amount or activity of miRNA-410 by contacting stem cells or downstream precursor cells with the test compound. Based on the disclosure herein, differentiation of the stem cells or downstream precursor cells into predominantly astrocytes indicates that the test compound increases the amount or activity of miRNA-410, and differentiation of the stem cells or downstream precursor cells into predominantly neurons and oligodendrocytes indicates that the test compound decreases the amount or activity of miRNA-410. For those test compounds that do not readily cross the cell membrane, those skilled in the art are aware of methods that can be used to introduce a compound into cells (e.g., electroporation, lipid-based delivery systems, and nanoparticle-based delivery systems).

Test compounds that decrease the amount or activity of miRNA-410 are candidate compounds for treating diseases in which stimulation of neurogenesis would be beneficial. Such diseases include, for example, lisencephaly, Rhett's syndrome, and hydrocephalitus. Similarly, test compounds that increase the amount or activity of miRNA-410 are candidate compounds for treating diseases in which the production of astrocytes is stimulated would be beneficial. Such diseases include, for example, lissencephaly and blood brain barrier dysfunction.

Methods of Treating Tumors

The disclosure herein identifying the role of miRNA-410 in the differentiation of stem cells or downstream precursor cells into populations that are predominantly astrocytes, oligodendrocytes, or neurons can be used in methods of treating tumors. For example, in one embodiment, the amount or activity of miRNA-410 can be decreased in a mammal having an astroglial tumor. Methods for decreasing the amount or activity of miRNA-410 are discussed herein and include, for example, the use of various oligonucleotides (e.g., antagomirs, 2-O-Me-RNA, morpholino oligonucleotides, and LNA oligonucleotides) or a miRNA sponge. Alternatively, a compound identified in a screening method as described herein can be used to decrease the amount or activity of miRNA-410 in a mammal having an astroglial tumor.

Representative astrocytic tumors include gliomas, astrocytomas (e.g., protoplasmic, gemistocytic, or fibrillary), glioblastomas multiforme, pilocytic astrocytomas, subependymal astrocytomas, pleomorphic xanthoastrocytomas, and neurofibromas. Decreasing the amount or activity of miRNA-410 in an astroglial tumor results in differentiation of the tumor into mature, non-proliferating type I or type II astrocytes.

In another embodiment, the amount or activity of miRNA-410 can be increased in a mammal having a neuronal tumor or oligodendrocyte tumors. Methods for increasing the amount or activity of miRNA-410 are discussed herein and include, for example, direct delivery of miRNA-410 or overexpression of a DNA encoding miRNA-410. Alternatively, a compound identified in a screening method as described herein can be used to increase the amount or activity of miRNA-410 in a mammal having a neuronal tumor or oligodendrocyte tumors.

Representative neuronal tumors include neuroblastomas, medulloblastomas, retinoblastomas, gangliocytomas, neurocytomas, and ependymoblastomas. Increasing the amount or activity of miRNA-410 in a neuronal tumor results in differentiation of the tumor into non-proliferating neurons. Representative oligodendrocyte tumors include oligoastrocytomas and oligodendrogliomas. Increasing the amount or activity of miRNA-410 in an oligodendrocyte tumor promotes differentiation of oligodendrocytes.

Any such compound that increases or decreases the amount or activity of miRNA-410 can be delivered to a tumor by any number of means including, but not limited to, injection into the tumor, intranasal delivery, intracranial delivery, and delivery via the optic nerve. Delivery of a compound to an astrocytic tumor, an oligodendrocyte tumor, or a neuronal tumor also can be via the cerebrospinal fluid (CSF) by delivery to the peripheral blood stream in combination with one or more agents that allow such compounds to cross the blood brain barrier, or in vivo electroporation (see, for example, Anwer, 2008, *Methods Mol. Biol.*, 423:77-89).

In addition to treating tumors, the amount or activity of miRNA-410 can be decreased at the site of a central nervous system (CNS) injury in order to inhibit the activation of astrocytes. Since astrocytes exhibit a reactive response upon damage to the CNS (e.g., spinal cord injury or traumatic brain injury (TBI)) and form scar tissue, inhibiting this activation of astrocytes by reducing the amount or activity of miRNA-410) can provide benefits in treating such injuries (e.g., ameliorating the damage from such injuries, diminishing the negative effects of such injuries, reducing the amount of scar tissue resulting from such injuries).

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1

Analysis of miRNA-410 Expression

Microarray analysis identified a microRNA, miR-410, from the subventricular zone (SVZ) of adult mice. MiR-410 is present in mammals, and the sequence is highly conserved in mouse, human, and multiple other mammalian species. It is present in a cluster of miRNAs (miR379-miR410), one of which (miR-134) is involved in stimulating dendritic outgrowth from hippocampal neurons by inhibiting translation of Pumilio2 mRNA. miR-410 was previously identified as expressed in the midgestation embryo, as a candidate nucleic acid for male pattern baldness, and in cell cycle control. The structure of the *Mus musculus* miR-410 is shown in FIG. 1. Using a conditional transgenic mouse in which noggin can be inducibly expressed in nestin+ neural stem cells, it was shown that miR-410 was significantly down-regulated relative to a control neural stem cells when the noggin transgene was overexpressed.

To validate the microarray data, quantitative RT-PCR (qRT-PCR) of induced and noggin-overexpressing SVZ was used. It was observed that miR-410 was down-regulated more than 15-fold in the induced SVZ (FIG. 2). Since miRNAs are short, and family members may differ by a single nucleotide, care was taken to ensure that only mature miRNA is assayed by PCR. To accomplish this, mature miRNAs were tail-polyadenylated with *E. coli* poly (a) polymerase prior to reverse transcription. An oligo-dT primer with a universal primer binding site linked to its 5' end was used during reverse transcription. During qRT-PCR, the universal primer and the miRNA-specific primer were employed to ensure that only mature miRNA was assayed. In situ hybridization analysis were used to confirm overexpression and inhibition of mature miR-410. Additional microarray analysis of RNAs from noggin-expressing and control cerebellar neural stem cells was performed. It was observed that the miRNA was similarly downregulated by noggin overexpression.

Figure 3:
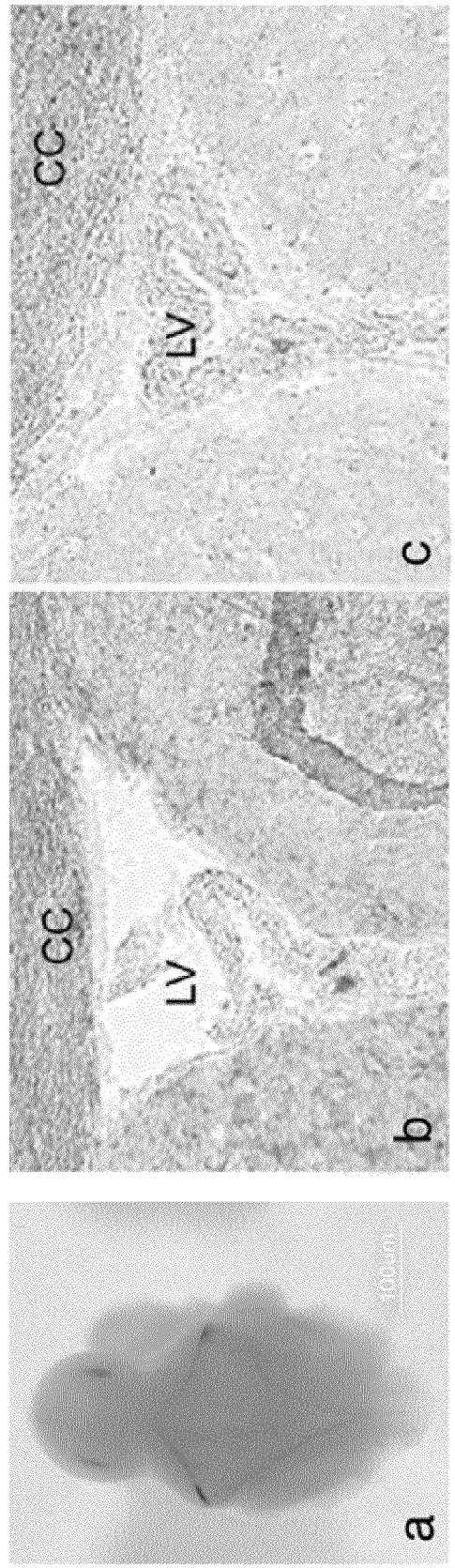
FIG. 3 is a series of images demonstrating expression of miR-410 (3A) in the CNS in E11.5 mouse embryos. In the adult mouse brain, it is expressed at high levels in the SVZ neural stem cell zone (3C).

In situ hybridization localizations of miRNA were performed during development and in the adult SVZ. During development, miR-410 was restricted to the nervous system, where it was expressed at high levels at the rhombic lip and midbrain at E11.5 (FIG. 3A). In the adult brain, miR-410 was expressed at high levels in the SVZ neural stem cell zone (FIG. 3B).

Figure 4:
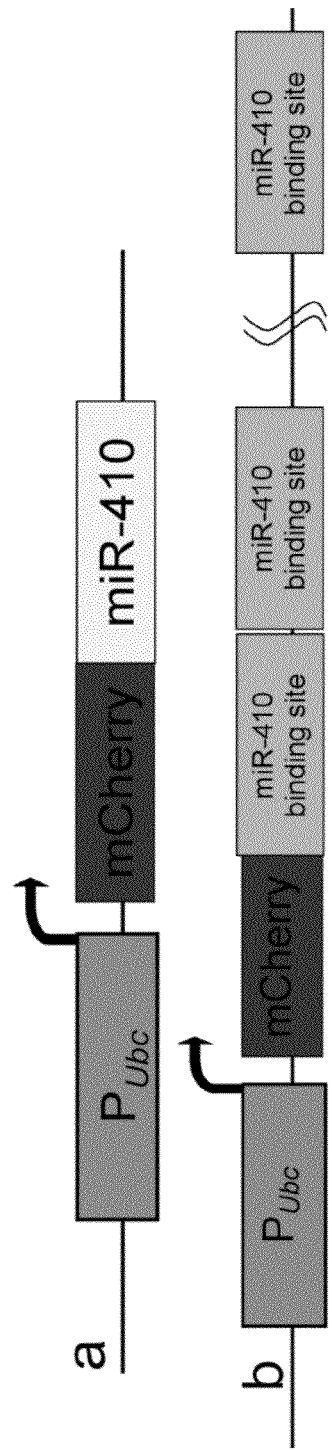
FIG. 4 is a schematic depicting a miR-410 over-expression vector (4A) and an expression construct where the ubiquitin promoter drives expression of a "sponge" in which six miR-410 binding sites are expressed downstream of mCherry (4B).

To inhibit and overexpress miR-410, two expression constructs were developed (FIG. 4). The backbone of each vector contains a puromycin cassette for selection and development of cell lines. The first construct (FIG. 4A) employed the Ubiquitin (Ubc) promoter to drive overexpression of mCherry and the miRNA. In the second construct (FIG. 4B), the Ubiquitin promoter drives expression of a "sponge" in which six miR-410 binding sites are expressed downstream of mCherry. Because miRNAs are highly conserved and short, and because miRNA families display close sequence identities, it is difficult to use small interfering RNA (siRNA) technology to target them. Other approaches include the use of antagomirs, which are small synthetic RNAs that are perfectly complementary to and which irreversibly bind the target miRNA. For strong, long-term inhibition, a new class of genetically encoded competitors of miRNAs was employed: the miRNA "sponge." These inhibitors are transcripts expressed from strong promoters, and they contain multiple tandem binding sites specific to the miRNA of interest, thus competing with the endogenous targets for the miRNA and de-repressing the targets.

Example 2

Analysis of miR-410-Expressing Embryonic Stem Cells

Figure 5:
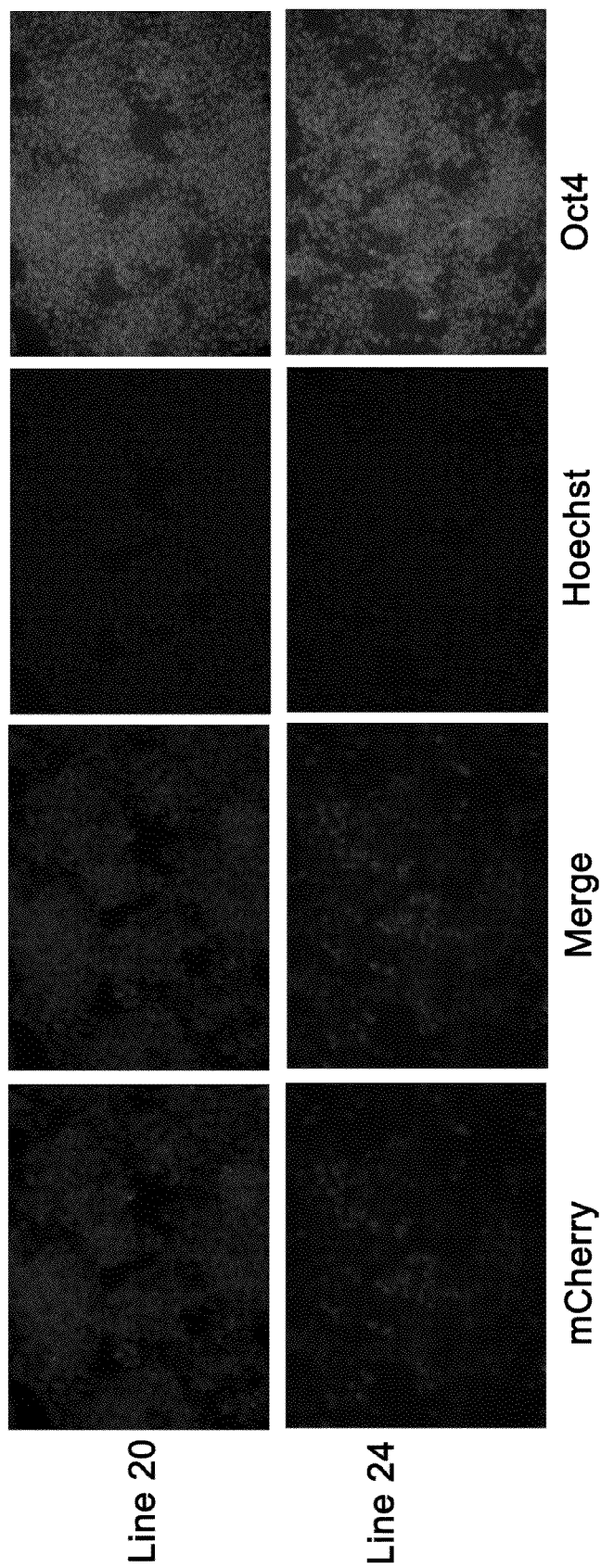
FIG. 5 is a series of images depicting mouse embryonic stem (ES) cell lines stably over-expressing miR-410 (indicated by mCherry) express the ESC marker Oct4 in control ES cell culture conditions.
Figure 6:
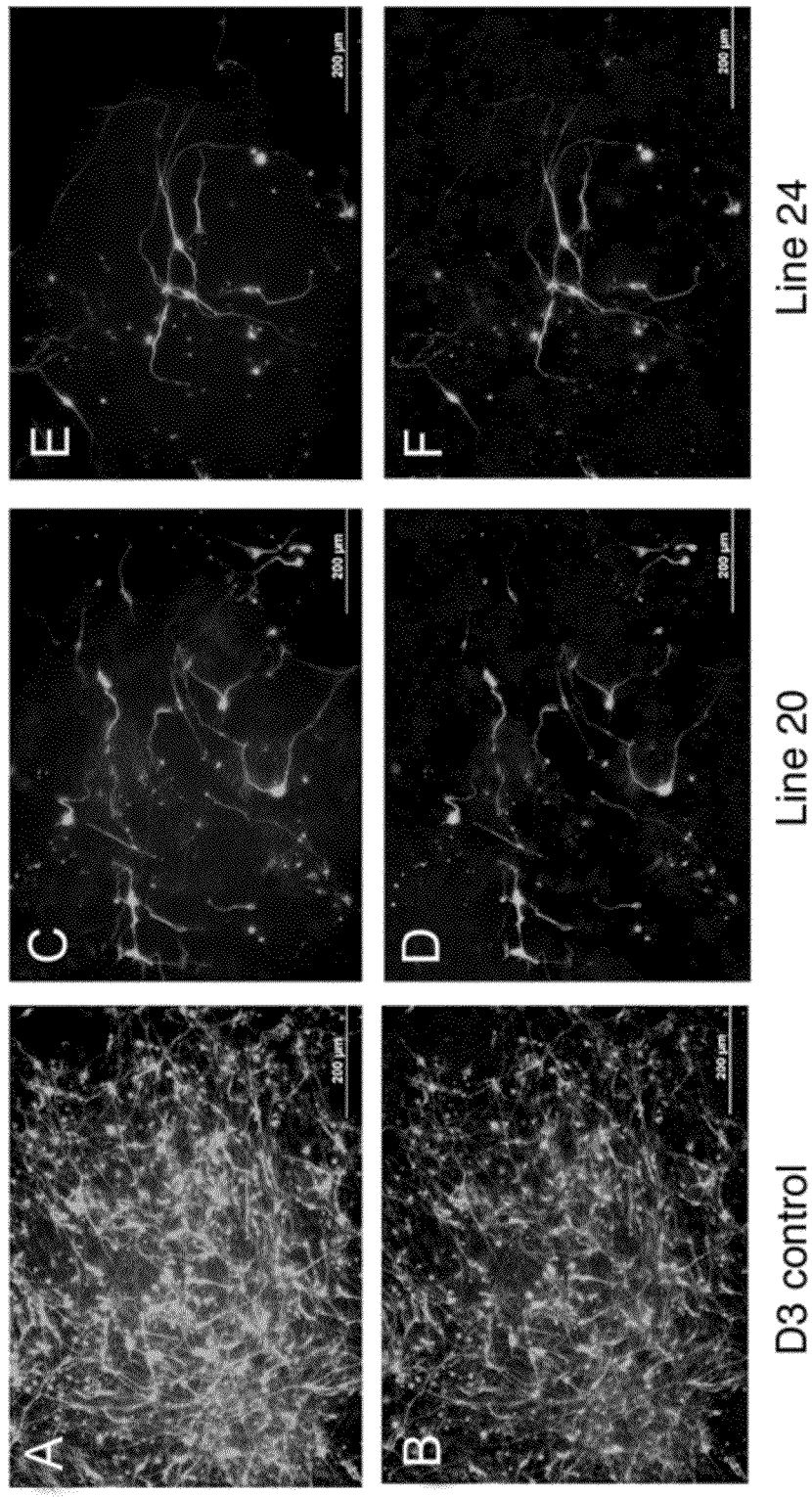
FIG. 6 is a series of images demonstrating widespread differentiation of Tuj1 positive neurons. (6A-B) After 6 days in vitro, control D3 cells differentiated widely into neurons (Tuj1+) whereas neuronal differentiation was abrogated in over-expressing ES cell line 20 (6C-D) and line 24 (6E-F). Tuj1: FITC; nuclei: Hoechst 33258.

To create mouse embryonic stem cell (mESC) lines stably expressing miRNA-410, D3 mESC were transfected with the expression construct from FIG. 4A using Lipofectamine 2000. mESC were selected in antibiotic and 12 cell lines were expanded and characterized. Two stable cell lines were selected for analysis, one in which miR-410 is overexpressed 7-fold (line 24) and another in which miR-410 is overexpressed 20-fold (line 20) relative to the parental D3 cell lines (see FIG. 5). Additional control lines expressed mCherry alone. Cell numbers were analyzed after 7 days of culture in complete medium. The cells behaved as embryonic stem cells, expressed Nanog and Oct4, and divided rapidly with no evidence of proliferation changes or apoptosis. When grown in neuronal differentiation conditions (N2:B27 defined medium with retinoic acid), there was widespread differentiation of Tuj1-positive neurons after 6 days in vitro in the control D3 line (FIGS. 6A and 6B), but not in lines expressing miRNA-410 (FIGS. 6C-D and 6E-F).

Figure 7:
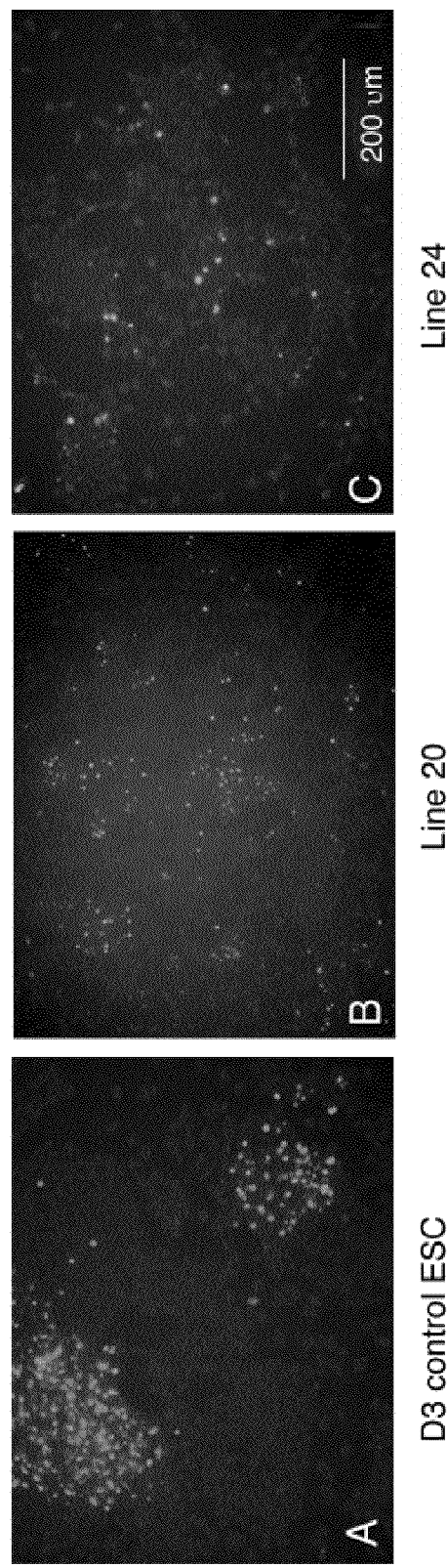
FIG. 7 is a series of images depicting TUNEL staining of control (7A) and miRNA-410 overexpressing lines 20 (7B) and 24 (7C).
Figure 8:
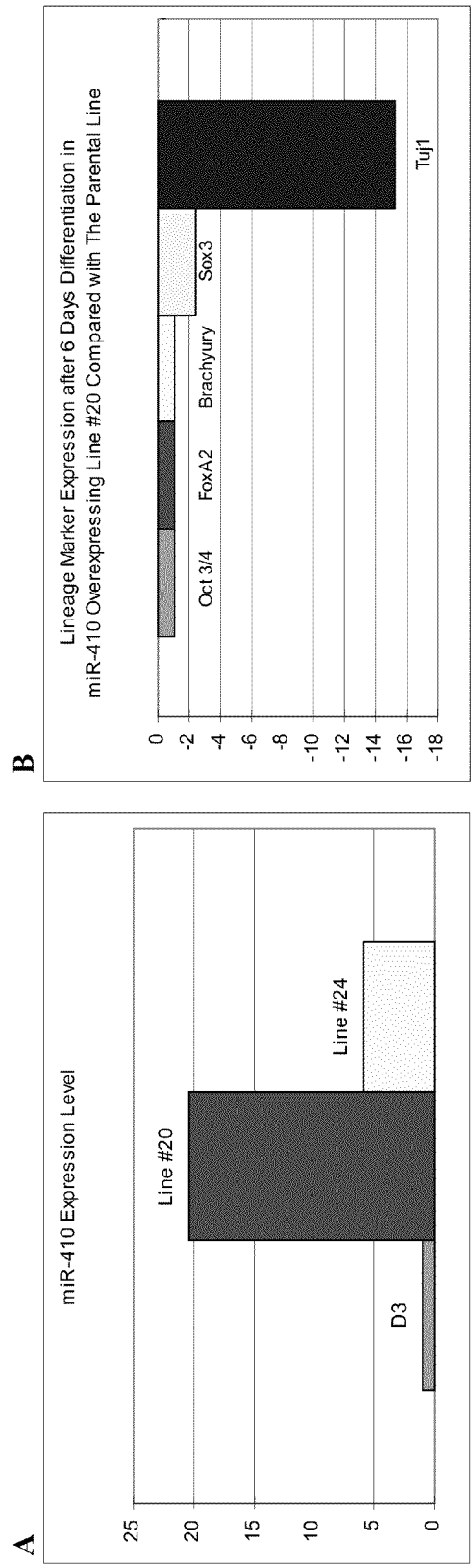
FIG. 8 is a set of bar graphs demonstrating that (8A) miRNA-410 is over-expressed 20-fold in line #20 and it is expressed 7-fold higher than in control cells in line #24. (8B) q-RT-PCR analysis showed that expression of an ESC marker (Oct4), an endoderm lineage marker (FoxA2), and a mesoderm lineage marker (Brachyury) were not affected, while neural lineage markers (Sox3 and Tuj1) were down-regulated by over-expression of miRNA-410.

To directly address the concern that miR-410 overexpression in embryonic stem cells may promote apoptosis, TUNEL staining was performed in vitro (FIG. 7). There was no significant difference between D3, control lines with mCherry alone, or in either line 20 or 24. qRT-PCR with lineage restricted markers was used to identify cells. In addition to the expected lineages, it is crucial to examine expression of ES markers (Oct3/4), markers of endoderm (FoxA2), and mesoderm (Brachyury) in ES cultures. Sox3 was employed for neural precursors and Tuj1 for early neurons. Analysis was done on Line 20 cells after 6 days in vitro and compared with the parent D3 line. When miRNA-410 is expressed 20-fold higher than in controls, expression of neuronal marker, Tuj1, was downregulated 15-fold (FIG. 8).

Example 3

Role of miR-410 in Neural Stem Cells

Figure 9:
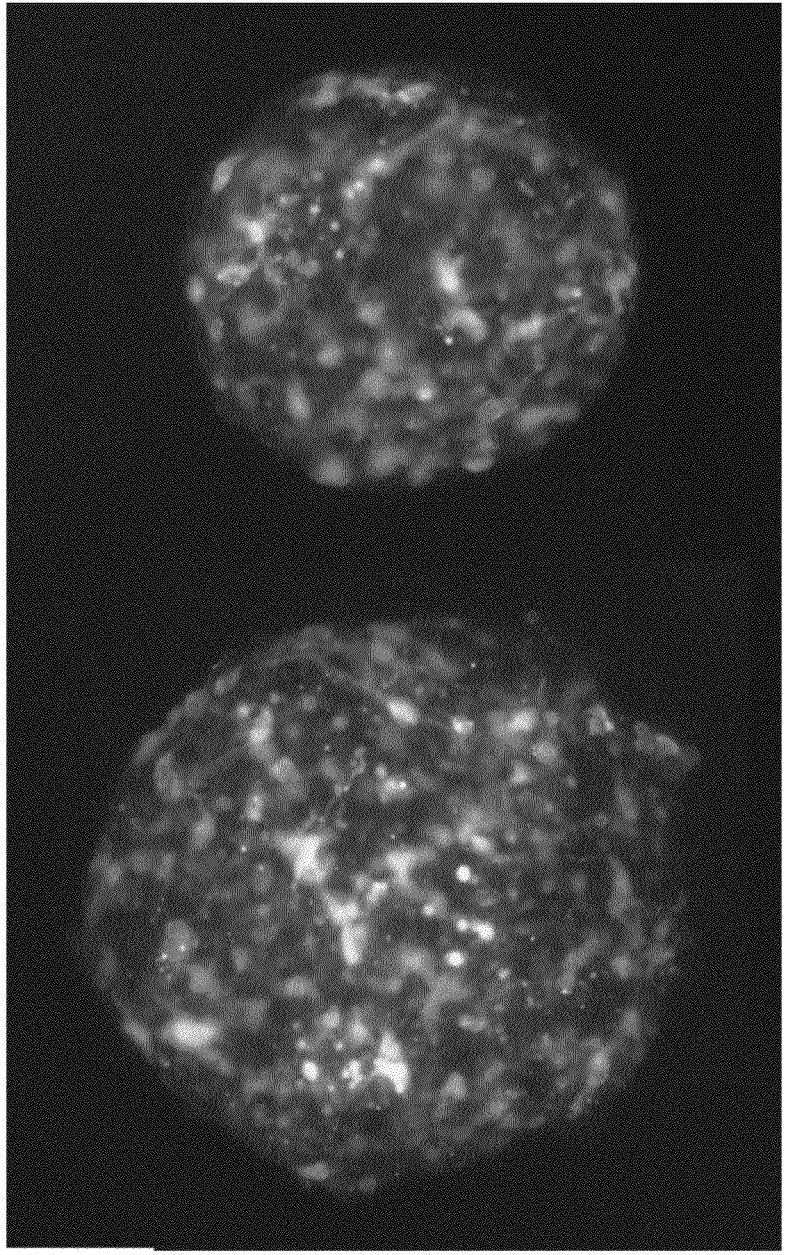
FIG. 9 is a photograph of spheres produced during differentiation of neuronal stem cells illustrating the persistent expression of mCherry and, therefore, the transgene.

To examine the role of miR-410 in neural stem cells from the adult brain, neurospheres were derived from adult SVZ, grown for 14 days in suspension culture with medium containing FGF2 and EGF, and then transfected with miR-410 expression, sponge, or control constructs. The vectors were expressed well and many uniformly-shaped red spheres were obtained (FIG. 9). Spheres were disaggregated and differentiated for 7 days in medium lacking growth factors but containing 1% serum. Immunohistochemical localization of cell type-specific antibodies was then carried out: GFAP (astrocytes), myelin basic protein (oligodendrocytes), and Tuj1 (neurons).

Figure 10:
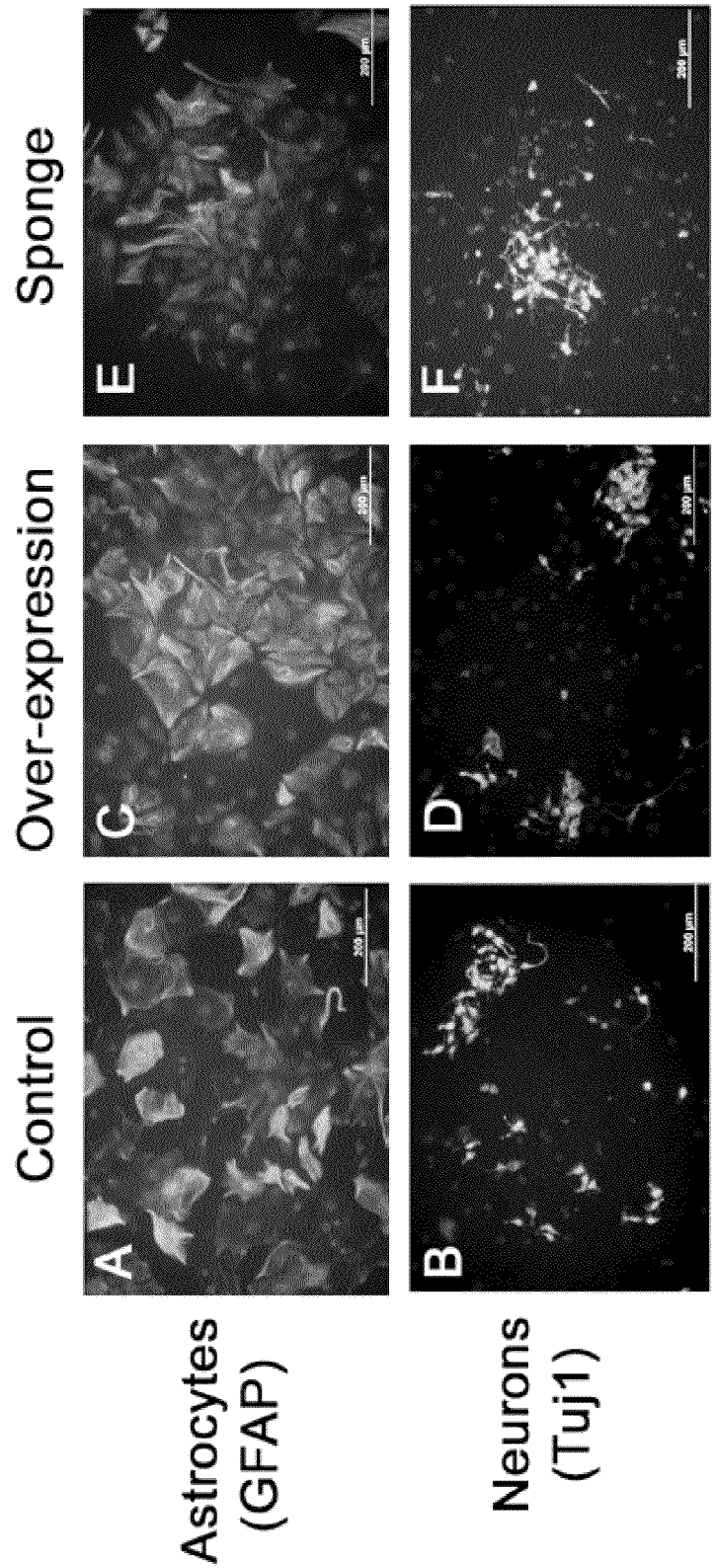
FIG. 10 illustrates the presence of astrocytes and neurons following over-expression of miRNA-410 (Panels C and D, respectively) and following the use of the microRNA sponge to inhibit miRNA-410 (Panels E and F, respectively) compared to control cells (Panels A and B, respectively).

It was observed that overexpression of miR-410 significantly decreased the number of neurons and oligodendrocytes present in these cultures. Astrocyte differentiation was increased, while inhibition using the sponge increased neuronal and oligodendrocyte differentiation to levels greater than controls and decreased astrocyte numbers (FIG. 10). Experiments were replicated in three independent experiments, each with three biological replicates. Cells were counted from five fields in each replicate (45 fields).

Figure 11:
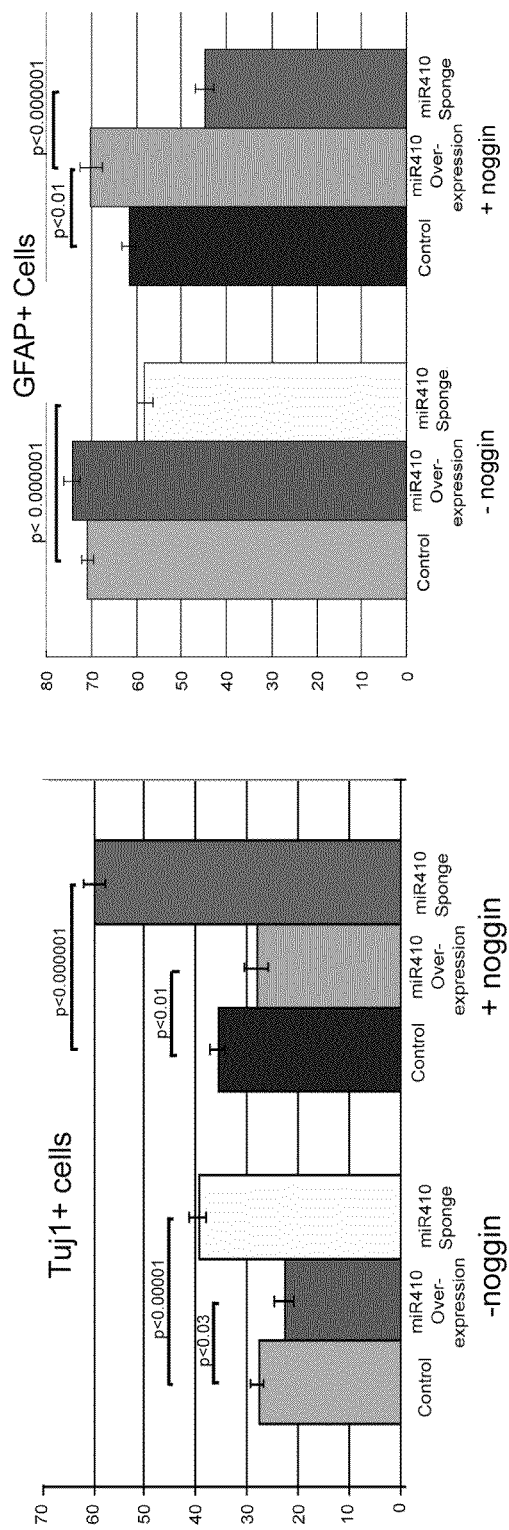
FIG. 11 is a set of bar graphs showing that the number of Tuj1-positive neurons was increased by miRNA-410 knock-down and decreased by the over-expression of miRNA-410. The number of GFAP-positive astrocytes was significantly decreased in cells transfected with miRNA-410 sponge, compared with controls. Furthermore, miRNA-410 over-expression rescued the increase in Tuj1-positive neurons and the reduction in GFAP-positive cells produced by noggin.

Quantitative analysis of cell numbers was carried out in differentiated neurosphere cultures with and without noggin protein. The number of Tuj1 positive neurons (FIG. 11, left panel) was significantly increased by miR-410 inhibition and significantly decreased by the overexpression of miR-410. miR-410 overexpression inhibited the differentiation of Tuj1 positive neurons produced by noggin while, in the presence of the sponge, noggin significantly increased neuronal differentiation to 60%.

Exposure of neural stem cells to the sponge significantly increased the numbers of myelin basic protein (MBP)-positive oligodendrocytes compared to control cultures. These results were sensitive to the presence of noggin proteins, either produced by transgene induction or addition of noggin protein to the medium.

Figure 12:
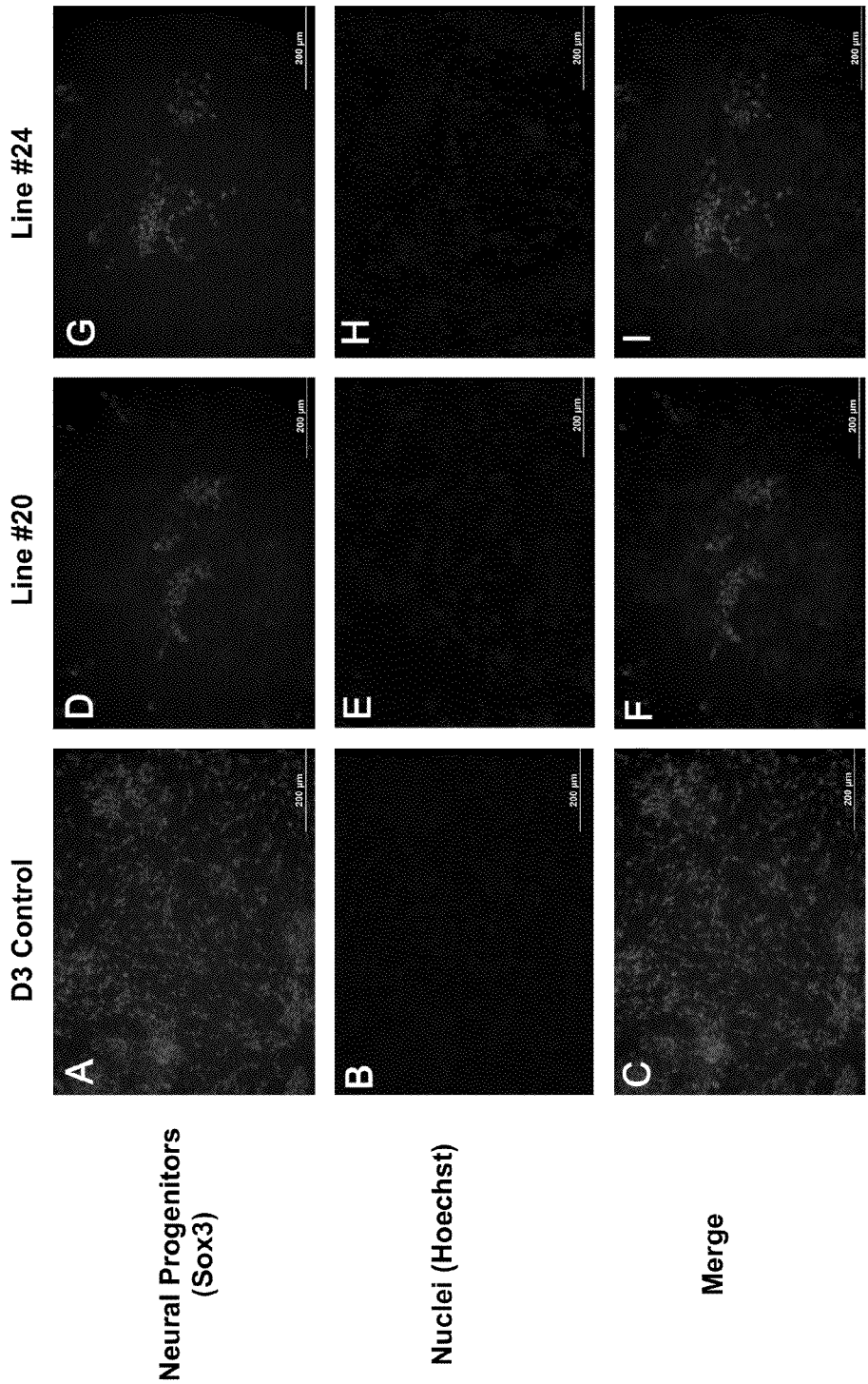
FIG. 12 is a series of images demonstrating that over-expression of miRNA-410 strikingly reduces the number of Sox3-positive neural precursors compared to the parental D3 ES cells.
Figure 13:
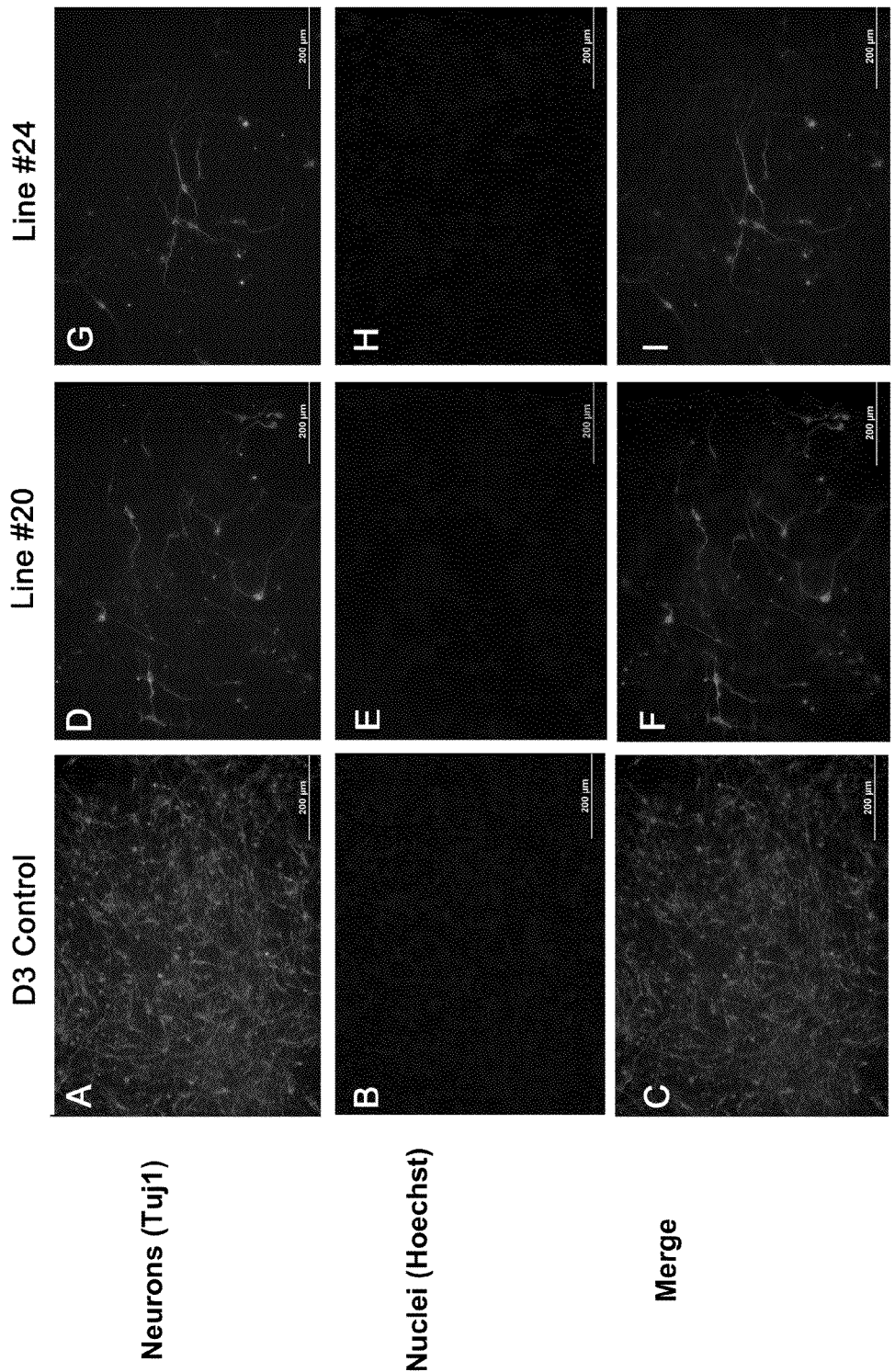
FIG. 13 is a series of images demonstrating that over-expression of miRNA-410 strikingly reduces the number of Tuj1-positive neurons compared to the parental D3 ES cells.
Figure 14:
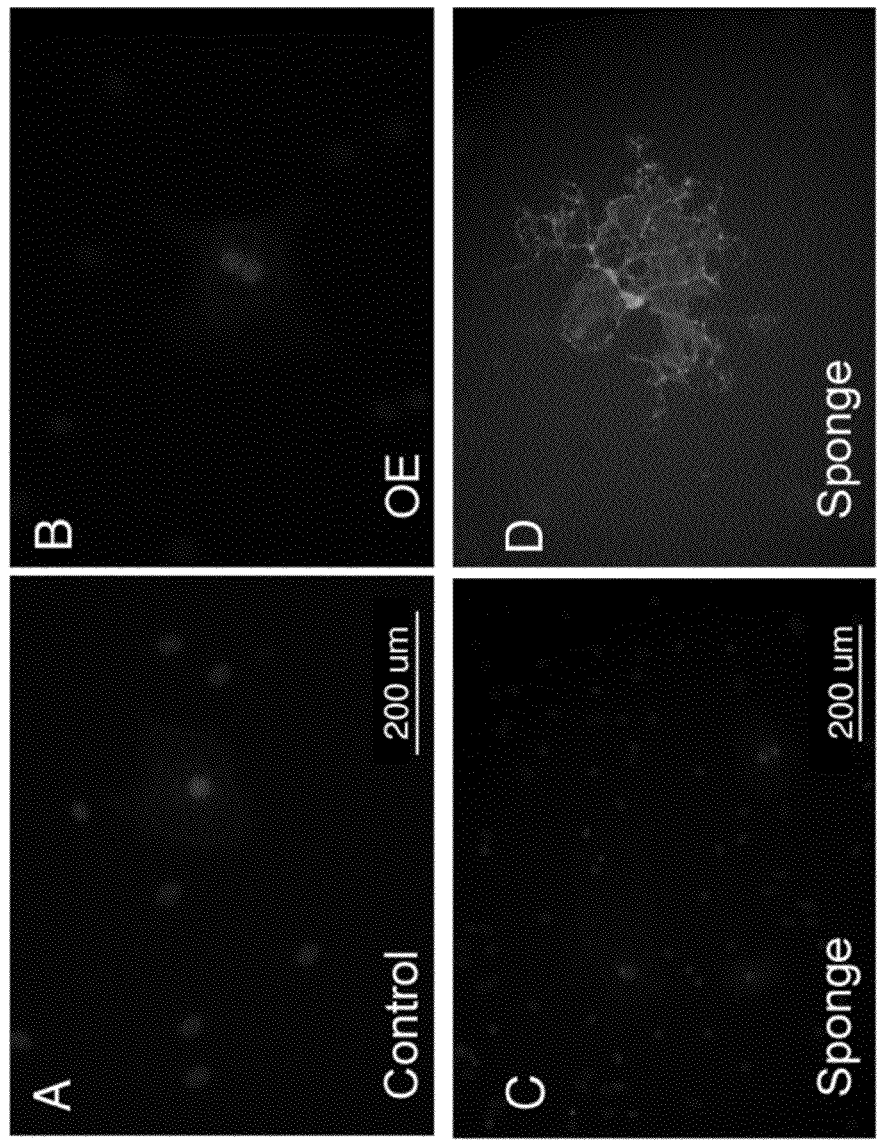
FIG. 14 illustrates the morphology of oligodendrocytes derived from the SVZ in control culture conditions (A), following miRNA-410 over-expression (B), and exposure to the sponge (C,D). The number and maturity of MBP+ oligodendrocytes was increased in the presence of the sponge (C), and particularly in the presence of noggin and the sponge.

The number of GFAP positive astrocytes (FIG. 11, right panel) was significantly reduced in cells transfected with the miR-410 sponge as compared with controls. miR-410 overexpression restored the noggin-promoted reduction in GFAP positive cells to control levels, while, in the presence of the miRNA sponge, noggin significantly reduced astrocyte numbers. In addition, in ES cells, over-expression of miR-410 reduces the number of Sox3-positive neural precursors (FIG. 12) and Tuj1+ positive neurons (FIG. 13) compared to the parental D3 ES cells.

TABLE 1

Selected Predicted Targets of miR-410

| | | |
|---|---|---|
| NM_009233 | Sox1 | *Mus musculus* SRY-box containing gene 1 (Sox1) |
| NM_001044386 | Zfx | *Mus musculus* zinc finger protein X-linked (Zfx), transcript variant |
| NM_001083316 | Pdgfra | *Mus musculus* platelet derived growth factor receptor alpha (Pdgfra) |
| NM_054043 | Msi2 | *Mus musculus* Musashi homolog 2 (*Drosophila*) (Msi2) |
| NM_172303 | Phf17 | *Mus musculus* PHD finger protein 17 (Phf17) |
| NM_009322 | Tbr1 | *Mus musculus* T-box brain gene 1 (Tbr1) |
| NM_053242 | Foxp2 | *Mus musculus* forkhead box P2 (Foxp2) |
| NM_010488 | ELAV | *Mus musculus* ELAV (embryonic lethal, abnormal vision, *Drosophila*)-like 4 (Hu antigen D) (Elavl4) |
| NM_001083967 | Tcf4 | *Mus musculus* transcription factor 4 (Tcf4) |
| NM_178880 | Son | *Mus musculus* Son DNA binding protein (Son) |
| NM_008702 | NLK | *Mus musculus* nemo like kinase (Nlk) |
| NM_021543 | Pcdh8 | *Mus musculus* protocadherin 8 (Pcdh8) |
| NM_027642 | Phf6 | *Mus musculus* PHD finger protein 6 (Phf6) |
| NM_001042660 | Smad7 | *Mus musculus* MAD homolog 7 (*Drosophila*) (Smad7) |
| NM_008008 | Fgf7 | *Mus musculus* fibroblast growth factor 7 (Fgf7) |
| NM_008665 | Myt1 | *Mus musculus* myelin transcription factor 1 (Myt1) |
| NM_008342 | Igfbp2 | *Mus musculus* insulin-like growth factor binding protein 2 (Igfbp2) |
| NM_020505 | Vav3 | *Mus musculus* vav 3 oncogene (Vav3) |
| NM_144841 | Otx2 | *Mus musculus* orthodenticle homolog 2 (*Drosophila*) (Otx2) |

Example 4

Effects of Increasing or Decreasing miR-410 on Differentiation

The neural stem cell/subventricular zone (NSC/SVZ) was dissected from adult mice lacking transgenic noggin gene expression (Uninduced; i.e., animals carried the noggin transgene but were not exposed to doxycycline to induce transgene expression), cells were disaggregated and grown in tissue culture in the presence of: no additives (+0), the microRNA sponge (+Sp), a miR-410 expression construct (+410), the noggin protein (+Nog), both the sponge and the noggin protein (+Sp +Nog), or both the mir-410 expression construct and the noggin protein (+410 +Nog). Additional animals were exposed to doxycycline in vivo to induce expression of the noggin transgene in the NSC/SVZ (Induced), followed by tissue culture in the presence of: no additives (+0), doxycycline to induce the transgene in culture (+I), the microRNA sponge (+Sp), the miR-410 expression construct (+410), the noggin protein (+Nog), both the miR-410 expression construct and the noggin protein (+410 +Nog), or both the sponge and the noggin protein (+Sp +Nog), and differentiation of the neural stem cells into astrocytes (Astros), neurons, or oligodendrocytes (Oligos) quantified. See Table 2 below. The number of astrocytes and neurons were counted and a mean percentage calculated from 45 fields from three independent experiments with three replicates. The numbers of oligodendrocytes in the uninduced control cultures was set as 100% and the effects of manipulations on oligodendrocyte differentiation expressed relative to control. Table 2.

Uninduced Group. In the presence of the microRNA sponge (+Sp), astrocyte differentiation was strikingly inhibited with a concomitant increase in neuron and oligodendrocyte differentiation, while over-expression of miR-410 (+410) promoted astrocyte and inhibited neuron and oligodendrocyte differentiation. Addition of the noggin protein to the cultures (+Nog) inhibited astrocyte differentiation and promoted neuronal and oligodendrocyte differentiation, which was further stimulated by the combination treatment of the noggin protein with the sponge (+Sp +Nog). On the other hand, over-expression of miR-410 in the presence of the noggin protein (+410 +Nog) was similar to no treatment.

Induced Group. When noggin expression was induced in vivo in the NSC/SVZ zone and then neural stem cells obtained and cultured (+0), there was an increase in neuronal and oligodendrocyte differentiation at the expense of astrocytes, compared with the uninduced group. When the transgene was induced in vivo followed by an additional in vitro induction (+I) this effect was augmented, as in cultures exposed to the miRNA sponge (+Sp). When miR410 was over-expressed in induced cells (+410), astrocyte differentiation was partially rescued, while addition of noggin protein (+Nog) was similar to transgene induction in vivo and in vitro (+I) but slightly less efficient in promoting neuronal differentiation than the miRNA sponge (+Sp). Addition of the noggin protein to miR-410 overexpressing cells (+410 +Nog) reverted differentiation to control (+0, Induced) levels, while addition of the noggin protein to cells expressing the microRNA sponge (+Sp +Nog) augmented their neuronal and oligodendroglial differentiation.

Overall, the data indicate that miR410 expression or over-expression inhibits neuronal and oligodendrocyte differentiation, which is rescued by noggin expression, while expression of the microRNA sponge promotes neuronal and oligodendrocyte differentiation, which can be further increased by the noggin protein.

TABLE 2

Effects of miRNA-410 on Differentiation

|  | Mean Astros ± sd |  | Mean Neurons ± sd | Mean Oligos ± sd | Mean % Oligos |
| --- | --- | --- | --- | --- | --- |
| Uninduced |  |  |  |  |  |
| +0 | 72.6 ± 1.6 | 1 | 27.3 ± 1.5 | 2.25 ± 0.4 | 100 |
| +Sp | 58.9 ± 1.6 | 3 | 41.1 ± 1.6 | 5.5 ± 0.2 | 244.4 |
| +410 | 77.6 ± 6.6 | 4 | 22.5 ± 0.9 | 1.8 ± 0.2 | 80 |
| +Nog | 62.5 ± 1.1 | 2 | 37.5 ± 1.1 | 4.5 ± 0.2 | 200 |
| +Sp +Nog | 54.2 ± 2.6 | 5 | 45.8 ± 2.6 | 6.7 ± 0.8 | 297.8 |
| +410 +Nog | 70.3 ± 1 | 6 | 29.6 ± 0.9 | 2.7 ± 0.8 | 120 |
| Induced |  |  |  |  |  |
| +0 | 65.3 ± 2.1 | 7 | 34.8 ± 2.1 | 4.3 ± 0.7 | 192 |
| +I | 55.1 ± 0.5 | 9 | 44.9 ± 0.5 | 6.7 ± 0.5 | 298 |
| +Sp | 53.5 ± 3.1 | 10 | 46.6 ± 3.1 | 7.3 ± 1.3 | 325.8 |
| +410 | 68.2 ± 0.2 | 11 | 31.8 ± 0.2 | 3.3 ± 0.2 | 148 |
| +Nog | 55.2 ± 0.6 | 8 | 44.8 ± 0.6 | 6.7 ± 0.5 | 298 |
| +410 +Nog | 65.5 ± 1.8 | 12 | 34.5 ± 1.8 | 4.7 ± 0.2 | 211.8 |
| +Sp +Nog | 51.3 ± 0.3 | 13 | 48.7 ± 0.3 | 7.8 ± 0.2 | 344.4 |

Example 5

Expression of miR-410 in Glioblastomas

RNAs were isolated from glioblastoma multiforme (GBM) specimens and from normal brain from the neurosurgery tumor bank at the University of Michigan and the amount of miR-410 was determined in qRT-PCR. Mature miRNAs were polyadenylated prior to reverse transcription. In qTR-PCR, the universal primer and the 410-specific primer were employed to ensure that only mature miRNA was quantified.

Figure 15:
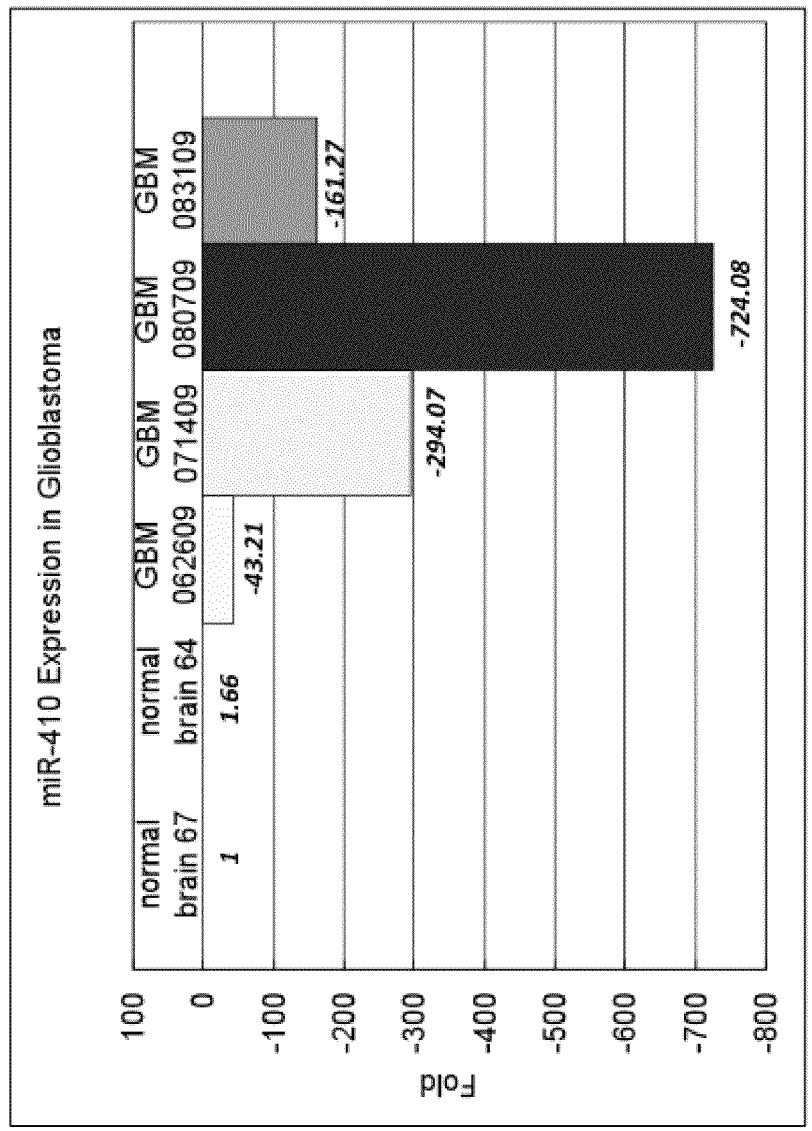
FIG. 15 is a graph showing the relative amount of miR-410 in glioblastomas.

Interestingly, expression of miR-410 was significantly down-regulated in all four GBM samples compared with samples from control brain (FIG. 15). Since GBM tumors contain both neurons and glial cells, GBM tumors likely represent an unusual situation with respect to miRNA-410. Although not bound by any particular theory, the results obtained herein with GBM samples are likely the result of the preponderance of neurons vs. glial cells in a particular GBM tumor.

Example 6

Luciferase Assays

The goal of these assays is to determine if the candidate target genes predicted in silico, are actually bound by miR-410. To do this, the 3'UTR of the target gene was cloned immediately downstream of the firefly luciferase ORF in the pmirGLO dual-luciferase vector (Promega, Wis.). Firefly luciferase is the primary reporter with an SV40 promoter driving *Renilla* luciferase to normalize expression. This construct was co-transfected with an miR-410 expression plasmid into HEK293 cells that do not express miR-410. Controls were vectors containing mutated miR-410 binding sites (mt). The expectation is that wild type (wt) reporters will have less activity than those with mutant sites if they are miR-410 targets.

Figure 16:
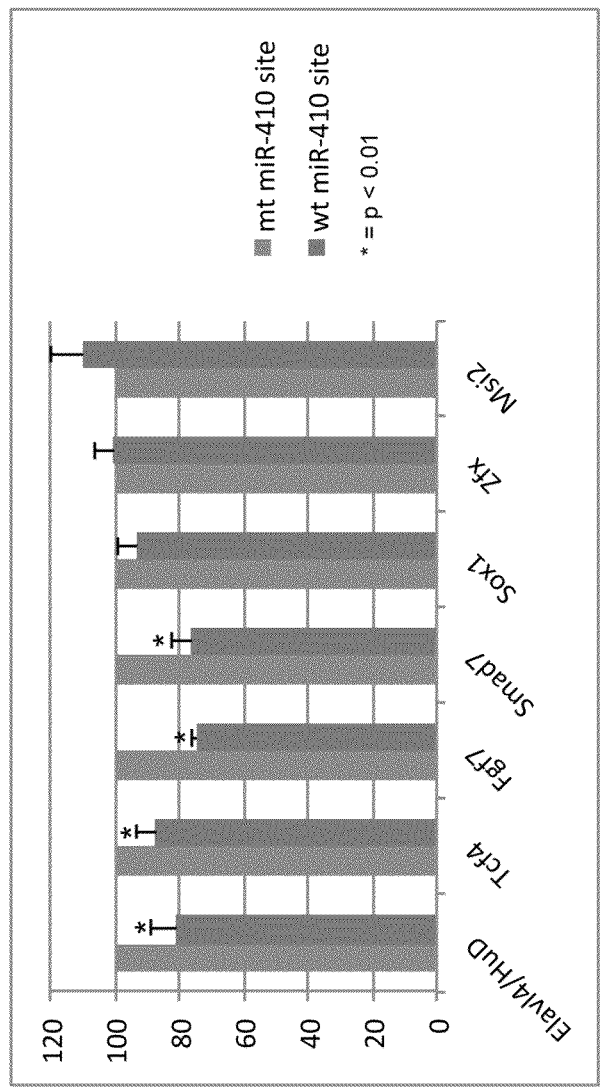
FIG. 16 is a graph showing reporter gene expression using wild type (dark gray bars) or mutant (light gray bars) miR-410 recognition sequences from the Elavl4/HuD, Tcf4, Fgf7, Smad7, Sox1, Zfx, and Msl2 genes.

Specifically, the 3'UTR of miR-410 target candidate genes was amplified by PCR and cloned into the pmirGLO plasmid between NheI and SalI sites according to the manufacturer's protocol. For genes with a 3'UTR shorter than 800 bp, the full length 3'UTR was cloned into the vector. For genes with a 3'UTR longer than 800 bp, a region at least 800 bp long containing the miR-410 site in the center was cloned. Vectors containing a 3'UTR with a mutated (mt, dark gray bars in FIG. 16) miR-410 site (TTAATTAA) were made using PCR based site-directed mutagenesis. HEK293 cells were co-transfected using Lipofectamine 2000; after 48 h, luciferase activity was measured in a luminometer. The results were standardized to *Renilla* expression (to control for transfection efficiency), with Firefly luciferase activity of controls with a mutated binding site set to 100 and wild type luciferase activity expressed as a percentage of control. Data from at least three independent experiments were then analyzed using Student's t-test.

Of the in silico predicted targets of miR-410, Elavl4, Tcf4, Fgf7 and Smad7 were significantly altered by miR-410, Sox1 was down-regulated at p<0.02, and Zfx and Msi2 were not altered. These data suggest that Elavl4, Tcf4, Fgf7, Smad7 and possibly Sox1 are, in fact, bound and regulated by miR-410. Confirmation by Western blot is performed. Biological function is probed further using over-expression and knock-down of the targets to determine the extent of differentiation of ESC and NSC.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An in vitro method of producing a population of predominantly astrocytes comprising:
    overexpressing miRNA-410 in a population of neural stem cells or neuronal or glial precursor cells and,
    culturing said cells,
    wherein said overexpressing miRNA-410 and said culturing results in differentiation of said cells into a population of predominantly astrocytes,
    thereby producing a population of predominantly astrocytes.

2. The method of claim 1, wherein said overexpressing miRNA-410 comprises introducing a nucleic acid molecule comprising a promoter operably linked to a DNA sequence encoding miRNA-410.

3. The method of claim 2, wherein the promoter is an inducible promoter.

4. An in vitro method of producing a population of predominantly astrocytes, comprising:
    transfecting a population of neural stem cells or neuronal or glial precursor cells with miRNA-410 RNA and,
    culturing said cells,
    wherein said transfecting and culturing results in differentiation of said cells into a population of predominantly astrocytes, thereby producing a population of predominantly astrocytes.

5. The method of claim 4, wherein the transfecting further comprises using a lipid-based delivery system.

* * * * *